United States Patent
Devanathan et al.

[11] Patent Number: 5,723,011
[45] Date of Patent: Mar. 3, 1998

[54] PROSTHETIC IMPLANT AND METHOD OF MAKING SAME

[75] Inventors: Thirumalai Devanathan, Warsaw; Steve T. Lin, Ft. Wayne, both of Ind.

[73] Assignee: Zimmer, Inc., Warsaw, Ind.

[21] Appl. No.: 219,247

[22] Filed: Mar. 28, 1994

Related U.S. Application Data

[63] Continuation of Ser. No. 994,018, Dec. 21, 1992, abandoned.
[51] Int. Cl.$^6$ ..................................................... A61F 2/28
[52] U.S. Cl. ................................................................ 623/16
[58] Field of Search ........................... 623/16, 18, 22, 623/23, 66; 228/178

[56] References Cited

U.S. PATENT DOCUMENTS

| | | | |
|---|---|---|---|
| 567,649 | 11/1896 | Hardwick | 228/178 |
| 4,589,883 | 5/1986 | Kenna | 623/22 |
| 4,636,219 | 1/1987 | Pratt et al. | 623/22 |
| 4,644,942 | 2/1987 | Sump | 623/16 |
| 4,650,109 | 3/1987 | Crivella et al. | 623/22 X |
| 4,660,755 | 4/1987 | Farling et al. | 228/178 |
| 4,693,721 | 9/1987 | Ducheyne | 623/16 |
| 4,813,965 | 3/1989 | Roberts | 623/16 X |
| 4,846,393 | 7/1989 | DeVillard | 228/178 |
| 4,863,475 | 9/1989 | Andersen et al. | 623/16 |
| 4,976,738 | 12/1990 | Frey | 623/23 |
| 4,997,445 | 3/1991 | Hodorek | 623/18 X |
| 5,013,324 | 5/1991 | Zolman et al. | 623/23 |
| 5,018,285 | 5/1991 | Zolman et al. | 29/465 |
| 5,068,020 | 11/1991 | Chu et al. | 204/192.15 |
| 5,139,528 | 8/1992 | Koch et al. | 623/66 |
| 5,219,363 | 6/1993 | Crowninshield et al. | 623/23 |

*Primary Examiner*—David Isabella
*Attorney, Agent, or Firm*—Todd A. Dawson

[57] ABSTRACT

This invention solves the above identified limitation by providing a prosthetic implant having a porous surface layer metallurgically bonded to the implant body, wherein a barrier film of metal is positioned between a portion of the porous surface layer and the implant body at areas of stress. By preventing bonding and thereby the formation of notches at strategic locations about the implant, the overall fatigue strength of the implant may be increased. In the preferred embodiment, the film of metal is formed from molybdenum which has a higher melting temperature than titanium which is commonly used for porous layers and the implant body.

By preventing notches at strategically significant areas about the implant, designers of prosthetic implants are less limited in the amount or location of the porous surface layer to be metallurgically bonded to the implant.

4 Claims, 2 Drawing Sheets

1

PROSTHETIC IMPLANT AND METHOD OF MAKING SAME

This application is a continuation of application Ser. No. 07/994,018 filed Dec. 21, 1992 abandoned.

FIELD OF THE INVENTION

This invention relates to a prosthetic implant having a porous surface layer metallurgically bonded to the implant body wherein a spacer prevents the metallurgical bond at locations of high stress.

BACKGROUND OF THE INVENTION

Prosthetic implants for the replacement of a portion of a patient's joints are well known. Likewise, it is well known to provide a porous surface layer on the implant to promote the ingrowth of bone and enhance fixation of the implant within the bone. The porous surface layer may take the form of a plurality of small beads or a wire mesh. Commonly, the porous surface layer is sintered or diffusion bonded to the implant. Sintering or diffusion bonding requires that the implant and porous surface layer be heated to a temperature sufficient to cause the porous surface layer and implant body to fuse or melt together at their point of mutual contact. Typically this temperature is around 1800 degrees Fahrenheit or 980 degrees Celsius. If the sintered or diffusion bonded junction were viewed in cross section, a small notch would be seen extending into the implant on each side of a contact point between the porous surface layer and the implant. These notches decrease the mechanical strength of the implant. To compensate for the effect of the notches and maintain the strength of the implant above the minimum guidelines established by the FDA of 18.9 ksi, the prosthetic implant manufacturer designs the implant to ensure that the resultant strength is well above the established minimum. This may require the porous surface layer be limited only to areas of large cross sections to meet the design strength criterion. Particularly, the designer is limited to the amount of porous surface layer attached to areas of high stress such as the proximal lateral wall of an orthopaedic hip stem implant.

SUMMARY OF THE INVENTION

This invention solves the above identified limitation by providing a prosthetic implant having a porous surface layer metallurgically bonded to the implant body, wherein a barrier film of metal is positioned between a portion of the porous surface layer and the implant body at areas of high stress. By preventing bonding and thereby the formation of notches at strategic locations about the implant, the overall fatigue strength of the implant may be increased. In the preferred embodiment, the film of metal is formed from molybdenum which has a higher melting temperature than titanium which is commonly used for porous layers and the implant body. In an alternative embodiment, instead of placing a film between the porous layer and the implant at locations of high stress, a section of the porous layer is entirely removed.

By preventing notches at strategically significant areas about the implant, designers of prosthetic implants are less limited in the amount or location of the porous surface layer to be metallurgically bonded to the implant.

It should be understood that the terms "metallurgical bond" or "metallurgically bonding" are used as common in the orthopaedic industry to indicate either a sintering or diffusion bonding process or a similar process wherein two metals are fused under high temperature and pressure.

Accordingly, it is an advantage of the invention to provide a method of attaching a porous metal surface to an implant body such that the formation of notches in the body can be eliminated from strategically significant portions of the implant.

Another advantage of the invention is in providing an implant having a porous surface attached thereto such that notches are not formed in areas of high mechanical stress.

Still other advantages of the invention will become apparent upon a reading of the following description taken with the accompanying drawings.

DESCRIPTION OF THE PREFERRED EMBODIMENTS

The preferred embodiments herein described are not intended to be exhaustive or to limit the invention to the precise forms disclosed. Rather, they are chosen and described to best explain the invention so that others skilled in the art might utilize their teachings.

Figure 1:
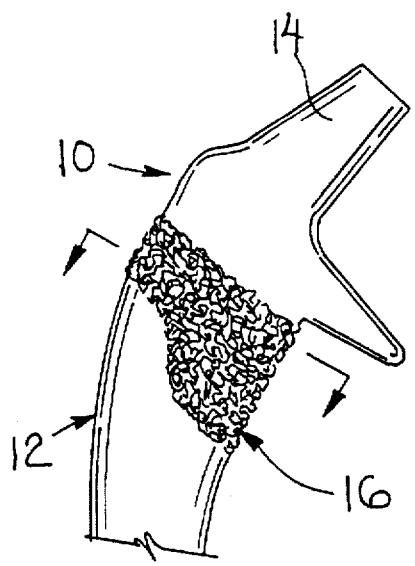
FIG. 1 is a partial elevational view illustrating a prior art hip stem implant having a porous surface layer attached.
Figure 2:
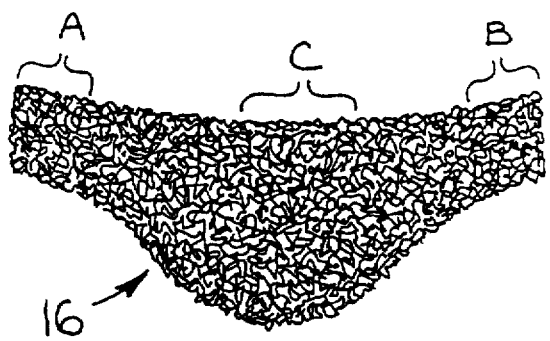
FIG. 2 is an elevational view of the porous fiber metal pad of the prior art.
Figure 3:
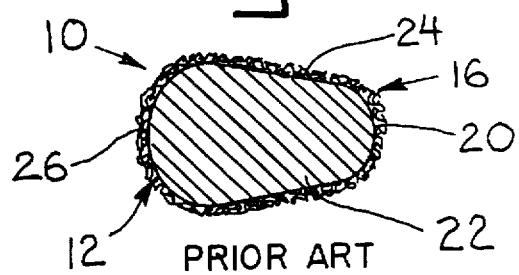
FIG. 3 is a cross sectional view taken along line 3—3 of FIG. 1.

FIGS. 1 and 3 illustrate a prior art orthopaedic implant in the form of a hip stem implant 10. Implant 10 includes a proximal body 12 and a distal stem (not shown). A neck 14 extends angularly from the proximal body 12 for accommodating an orthopaedic femoral head (also not shown). Proximal body 12 includes a medial wall 20, anterior and posterior walls 22 and 24, and a lateral wall 26 (see FIG. 2). A porous layer 16 is wrapped around the proximal body 12 of implant 10 and provides a structure for bone growth when implanted. Porous layer 16 as illustrated in the preferred embodiment is formed from a fiber metal mesh as is known in the industry. The porous layer 16 is metallurgically bonded to the implant body by a sintering or diffusion bonding process. This process causes the contacting portions of the porous layer 16 and the implant body 12 to fuse together. During the process, small notches are formed on each side of a fusion point. These notches reduce the mechanical strength of the implant requiring the designer to limit the amount of porous surface layer to maintain the implant strength above acceptable minimums. The limitation not only effects the quantity of porous layer attached to the implant but also the location of the porous layer on the implant. For example, with reference to implant 10 and porous layer 16, the amount of porous material attached to the lateral wall 26 of the implant proximal body 12 is limited. It is known that the lateral proximal wall 26 of an orthopaedic hip stem 10 is placed under a high tension load in use. Therefore, to create a safe implant, the amount of notches formed by bonding the porous surface layer is limited by limiting the amount of area covered by the porous layer 16 along the proximal lateral wall 26 (see FIG. 1). FIG. 2 illustrates the prior art porous surface layer 16 as a flat sheet prior to wrapping around the implant 10 to better illustrate the limited area covered by the layer 16. As illustrated in FIG. 2, the layer 16 is wrapped around the proximal body of the implant such that sections designated A and B are positioned in contact with the proximal lateral wall 26. Section C is positioned adjacent medial wall 20.

Figure 5:
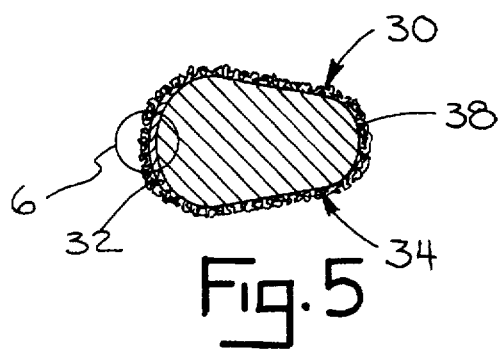
FIG. 5 is a cross section of an orthopaedic hip stem implant of the invention having a thin film positioned between the porous surface layer and posterior lateral wall of the implant body.
Figure 6:
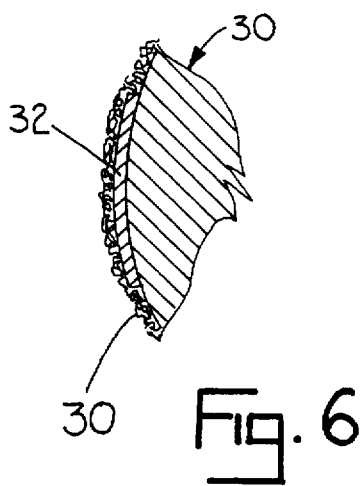
FIG. 6 is an enlarged cross sectional view of the area circled in FIG. 5 and designated by reference numeral 6.
Figure 4:
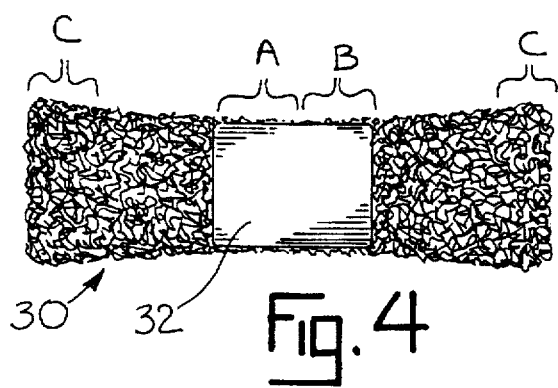
FIG. 4 is a view of the porous fiber metal pad of the invention including the metal film attached thereto.

The preferred embodiment and method of the invention are illustrated in FIGS. 4–6. As illustrated, the porous layer 30 is generally rectangular in shape and includes section C and section A and B. In the preferred embodiment of the invention, sections A and B are covered by a thin metal layer 32 formed from a metal having a higher melting temperature than the metal forming the porous layer 30 and the implant body. In the preferred embodiment, the metal layer 32 is formed from molybdenum. The porous layer 30 is wrapped around the body 34 such that the metal sheet 32 is positioned adjacent the lateral proximal side wall 36 as shown in FIGS. 5 and 6. As shown, so wrapped, sections C of porous layer 32 will meet adjacent the medial wall 38 of implant 30. The implant 34 and porous layer 30, with metal layer 32 positioned therebetween, are bonded together using a known sintering process. However, unlike the prior art implants as illustrated in FIGS. 1 and 2, the metal layer 32 will prevent the porous layer 30 from bonding to the implant body and thereby eliminate the formation of notches in the proximal lateral wall of the implant. FIG. 6 illustrates the junction between porous layer 30, metal layer 32 and the implant.

Figure 7:
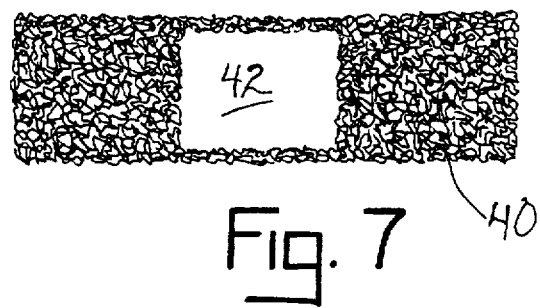
FIG. 7 is an alternative embodiment of the porous surface layer of the invention.

FIG. 7 illustrates the alternative embodiment of the invention wherein a portion of the porous layer 40 is cut out of the layer leaving an opening 42 to limit the formations of notches in an area of high stress on the implant. The layer 40 is formed such that the opening 42 would be positioned adjacent a high stress area on an implant.

It should be understood that while the invention has been described in association with a prosthetic hip stem implant, such should not be considered a limitation. The invention is easily adaptable to accommodate a wide variety of orthopaedic implants having a metallurgically bonded porous surface layer.

Further, it should be understood that the invention is not to be limited to the precise forms disclosed but may be modified within the keeping of the appended claims.

I claim:

1. A method of making a prosthetic implant having a metal body with a metal porous surface layer metallurgically bonded to said metal body with the metallurgical bond prevented at predetermined locations relative to said metal body, said method comprising the steps of;

a) providing a prosthetic implant having a metal body, said metal body having a predetermined location of high stress;

b) providing a porous layer formed from a first metal;

c) metallurgically bonding said porous layer to the metal body such that said porous layer and;

d) providing means for preventing the porous layer from bonding with the metal body at said predetermined location of high stress.

2. The method of claim 1 wherein steps c and d further includes the steps of;

a) bonding a thin layer of a second metal to a portion of said porous layer;

b) positioning said porous layer about said implant such that said thin layer is adjacent said predetermined location of high stress;

c) metallurgically bonding said porous layer to said metal body, wherein said thin layer of said second metal has a melting temperature higher than a melting temperature of said porous layer and said metal body such that metallurgical bonding is prevented at said predetermined location of high stress.

3. A method of making a prosthetic implant having a metal body with a metal porous surface layer metallurgically bonded to said metal body with the metallurgical bond prevented at predetermined locations relative to said metal body, said method comprising the steps of:

a) providing a prosthetic implant having a metal body, said metal body having a predetermined location of high stress;

b) providing a porous layer formed from a first metal;

c) metallurgically bonding a portion of said porous layer to the metal body, and;

d) providing means for preventing the porous layer from bonding with the metal body at said predetermined location of high stress.

4. The method of claim 3 wherein step c and d further include the steps of:

a) bonding a thin layer of a second metal to a portion of said porous layer;

b) positioning said porous layer about said implant such that said thin layer is adjacent said predetermined location of high stress;

c) metallurgically bonding said porous layer to said metal body, wherein said thin layer of said second metal has a melting temperature higher than a melting temperature of said porous layer and said metal body such that metallurgical bonding is prevented at said predetermined location of high stress.

* * * * *